United States Patent
Kim

(10) Patent No.: US 9,649,252 B2
(45) Date of Patent: May 16, 2017

(54) VARIABLE CAPSULE-TYPE HOT-AIR BATH APPARATUS

(71) Applicant: Tae Won Kim, Wonju-si (KR)

(72) Inventor: Tae Won Kim, Wonju-si (KR)

(73) Assignee: Tae Won Kim, Wonju-si (KR)

( * ) Notice: Subject to any disclaimer, the term of this patent is extended or adjusted under 35 U.S.C. 154(b) by 109 days.

(21) Appl. No.: 14/443,743

(22) PCT Filed: Nov. 7, 2013

(86) PCT No.: PCT/KR2013/010045
§ 371 (c)(1),
(2) Date: May 19, 2015

(87) PCT Pub. No.: WO2014/088217
PCT Pub. Date: Jun. 12, 2014

(65) Prior Publication Data
US 2015/0342827 A1    Dec. 3, 2015

(30) Foreign Application Priority Data

Dec. 7, 2012    (KR) .......................... 10-2012-0141698

(51) Int. Cl.
*A61H 33/06* (2006.01)
*A61H 33/00* (2006.01)
*A61F 7/00* (2006.01)

(52) U.S. Cl.
CPC ......... *A61H 33/066* (2013.01); *A61F 7/0053* (2013.01); *A61H 33/6005* (2013.01);
(Continued)

(58) Field of Classification Search
CPC .. A61H 33/06; A61H 33/066; A61H 33/6005; A61H 2203/0456;
(Continued)

(56) References Cited

U.S. PATENT DOCUMENTS 2,184,418 A * 12/1939 Faigle .................. A61G 13/009
                                                      312/139
2,308,452 A *  1/1943 Ortyl ....................... A47K 3/32
                                                        4/603
(Continued)

FOREIGN PATENT DOCUMENTS

JP        2003245326        9/2003
KR    2020000021510        12/2000
(Continued)

OTHER PUBLICATIONS

International Search Report—PCT/KR2013/010045 dated Mar. 11, 2014.

*Primary Examiner* — J. Casimer Jacyna
(74) *Attorney, Agent, or Firm* — Cantor Colburn LLP

(57) ABSTRACT

A variable capsule-shaped hot-air bath apparatus, includes: a first hot-air bath including a first cover covering and protecting an upper part thereof, a first film heater attached to a lower part of the first cover, a first frame attached and fixed to a circumference of one side of the lower part of the first cover and formed in a U-shape, legs coupled to the lower part of one side of the first frame, and wheels coupled to lower parts of the legs; and a second hot-air bath including a second cover covering and protecting an upper part thereof, a second film heater attached to a lower part of the second cover, a second frame attached and fixed to a circumference of one side of the lower part of the second cover, rail parts mounted on and fixed to inner sides of both sides of the second frame for smooth movement.

6 Claims, 7 Drawing Sheets

(52) U.S. Cl.
CPC  *A61F 2007/0088* (2013.01); *A61H 2033/061* (2013.01); *A61H 2201/10* (2013.01); *A61H 2203/0456* (2013.01)

(58) Field of Classification Search
CPC .......... A61H 2201/10; A61H 2033/061; A61F 7/0053; A61F 2007/0088; A47K 3/06; A47K 3/125; A47K 3/32; A47K 3/325
USPC ..................................... 4/535, 536, 526–530
See application file for complete search history.

(56) References Cited

U.S. PATENT DOCUMENTS

| | | | | |
|---|---|---|---|---|
| 3,741,218 | A * | 6/1973 | Novak | ................... A61H 33/06 607/91 |
| 6,549,809 | B2 * | 4/2003 | Ono | ...................... A61F 7/0053 4/536 |
| 6,613,071 | B1 * | 9/2003 | Fujii | ......................... A61N 5/06 607/91 |
| 6,886,386 | B1 * | 5/2005 | Cantrell | ................. B21D 37/14 483/29 |

FOREIGN PATENT DOCUMENTS

| | | | |
|---|---|---|---|
| KR | 1020020035806 | | 5/2002 |
| KR | 200305783 | | 2/2003 |
| KR | 1020070064070 | | 6/2007 |
| KR | 1020090051472 | | 5/2009 |
| WO | WO 2012/070696 | * | 5/2012 |

* cited by examiner

VARIABLE CAPSULE-TYPE HOT-AIR BATH APPARATUS

TECHNICAL FIELD

The present invention relates to a variable capsule-type hot-air bath apparatus, and more particularly, to a variable capsule-type hot-air bath apparatus, which is usable in various places, such as a bathhouse, an aesthetic message shop, and home, is simply assembled and manufactured, and is easily operated by anyone, thereby enabling a user to efficiently and safely take a hot-air bath through a whole body.

BACKGROUND ART

In general, as a life environment has been recently and rapidly developed by industrial development and economic growth, interest in health has been increased day by day, and a hot-air bath apparatus has been widely used as a means for solving adult diseases or stress of modern people.

A use of a hot-air bath has been increased day by day for the purpose of solving fatigue, releasing stiff muscles, and the like.

In this respect, a long of hot-air bath apparatus has been developed, among the development hot-air bath apparatuses, Korean Utility Model No. 0305783 discloses a hot-air bath apparatus, in which a bed-type mat mounted with a carbon fiber heating substance is combined with a semicircular hot-air bath apparatus, and the semicircular hot-air bath apparatus 2 is mounted on rails 6, which may transfer the semicircular hot-air bath apparatus 2, formed at both sides of the bed-type mat 4, so that a user may transfer the semicircular hot-air bath apparatus 2 over a whole body, and an infrared lamp is mounted at a border of a bottom surface of the bed-type mat 4 and tempered glass 8 is laid on the bed-type mat 4 (see FIG. 1).

In the hot-air bath apparatus, the semicircular hot-air bath apparatus is transferred in an up direction and a down direction on the mat, so that a user cannot hot-air bath over a whole body, and a product, such as tempered glass, is mounted on the upper part of the mat, so that the mat is heavy and thus it is difficult to move the mat.

As another related art, Korean Patent No. 10-457358 discloses a hot-air bath apparatus, including: a lower body 10 having a hollow inner side; a center body 11 coupled to an upper surface of the lower body 10 and divided into three spaces by a partition wall; a capsule member 12 coupled to the center body by a gas cylinder 17 to be opened and closed while one side thereof is rotated; a message means formed inside the lower body 10 to move along a rail in front and back directions and vibrate; a hot-air bath member which is formed in both side spaces of the center body 11, formed in multiple layers, and connected to an external power supply to heat and radiate far infrared ray, and move radiated hot-air to an upper side to enable a user to take a hot-air bath on a body; a mat 14 accommodated in a center space of the center body 11 to be in contact with a body; a flow space which is formed on an upper part of the capsule member 12 and has a hollow inner side, so that air flows therein; and a thermal means formed in the flow space to circulate hot-air into the capsule member 120 and radiate infrared rays (see FIG. 2).

The hot-air bath apparatus has the capsule type covering a whole body, so that it is complex to use the hot-air bath apparatus, the hot-air bath apparatus is large and heavy, and is considerably inappropriate to be used at home, it is not easy to manufacture and move the hot-air bath apparatus, a price of the hot-air bath apparatus is high, and thus it is not easy to generally use the hot-air bath apparatus at home.

DISCLOSURE

Technical Problem

The present invention has been made in an effort to solve the above-mentioned problems, and provides a variable capsule-type hot-air bath apparatus, which is usable in various places, such as a bathhouse, an aesthetic message shop, and home, an assembling time of which is decreased with a simple component, cost of which is decreased, and which enables a user to safely take a hot-air bath.

Technical Solution

In accordance with an aspect of the present invention, there is provided a variable capsule-shaped hot-air bath apparatus, including: a first hot-air bath apparatus 100 including a first cover 110 covering and protecting an upper part thereof, a first film heater 120 attached to a lower part of the first cover 110 to generate heat, a first frame 140 attached and fixed to a circumference of one side of the lower part of the first cover 110 and formed in a U-shape, legs 150 coupled to the lower part of one side of the first frame by using bolts, and wheels 160 coupled to lower parts of the legs by using bolts; and a second hot-air bath apparatus 200 including a second cover 210 covering and protecting an upper part thereof, a second film heater 220 attached to a lower part of the second cover 210 to generate heat, a second frame 240 attached and fixed to a circumference of one side of the lower part of the second cover and formed in a U-shape, rail parts 230 mounted on and fixed to inner sides of both sides of the second frame 240 to make the second hot-air bath apparatus 200 smoothly move, legs 150 coupled to a lower part of one side of the second frame by using bolts, and wheels 160 coupled and fixed to the lower parts of the legs 150 by using bolts.

Advantageous Effects

The present invention may be used in various places, such as a bathroom, an aesthetic message shop, and home, enables a user to take a hot-air bath for a whole body and a partial body with a simple operation method of a temperature controller, it is possible to easily and simply manufacture and assemble the present invention, thereby reducing costs, and enables a user to safely and effectively take a hot-air bath.

[Explanation of Reference Numerals and Symbols]

| | |
|---|---|
| 100: First hot-air bath apparatus | |
| 110: First cover | |
| 120: First film heater | 130: Temperature controller |
| 140: First frame | 141: First U-shaped frame |
| 142: First support | 143: Guide groove |
| 144: Roller | 150: Leg |
| 160: Wheel | 200: Second hot-air bath apparatus |
| 210: Second cover | 220: Second film heater |
| 230: Rail part | 231: Rail |
| 232: Guide | 233: Support plate |
| 234: Fixed frame | 240: Second frame |
| 241: Second U-shaped frame | |

BEST MODE

Mode for Invention

Hereinafter, an exemplary embodiment of a variable capsule-type hot-air bath apparatus of the present invention will be described with reference to the accompanying drawings.

Figure 1:
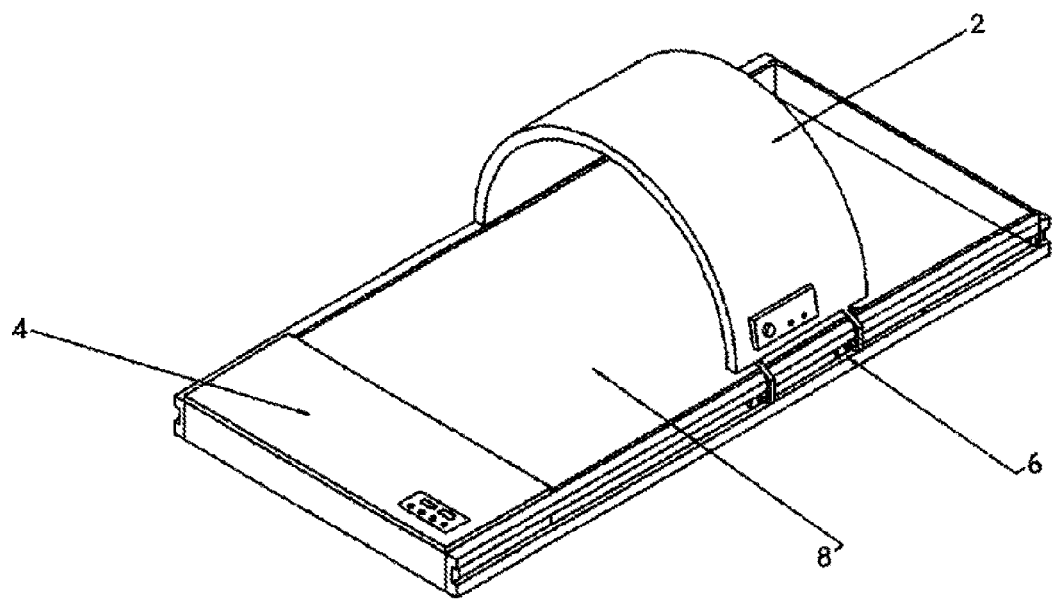
FIG. 1 is a perspective view of a related art of the present invention.
Figure 2:
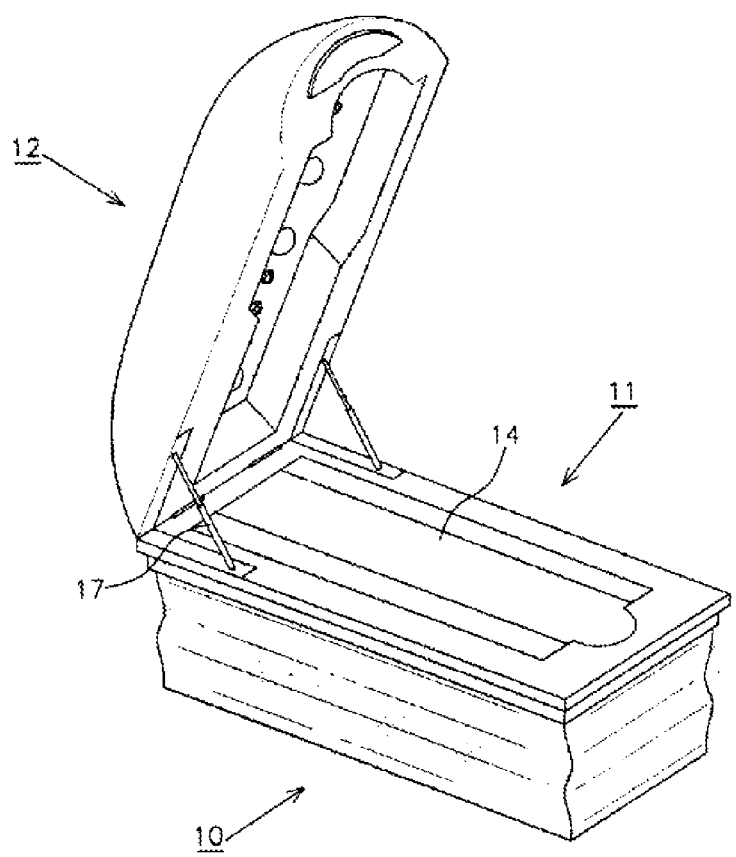
FIG. 2 is a perspective view of another related art of the present invention.
Figure 3:
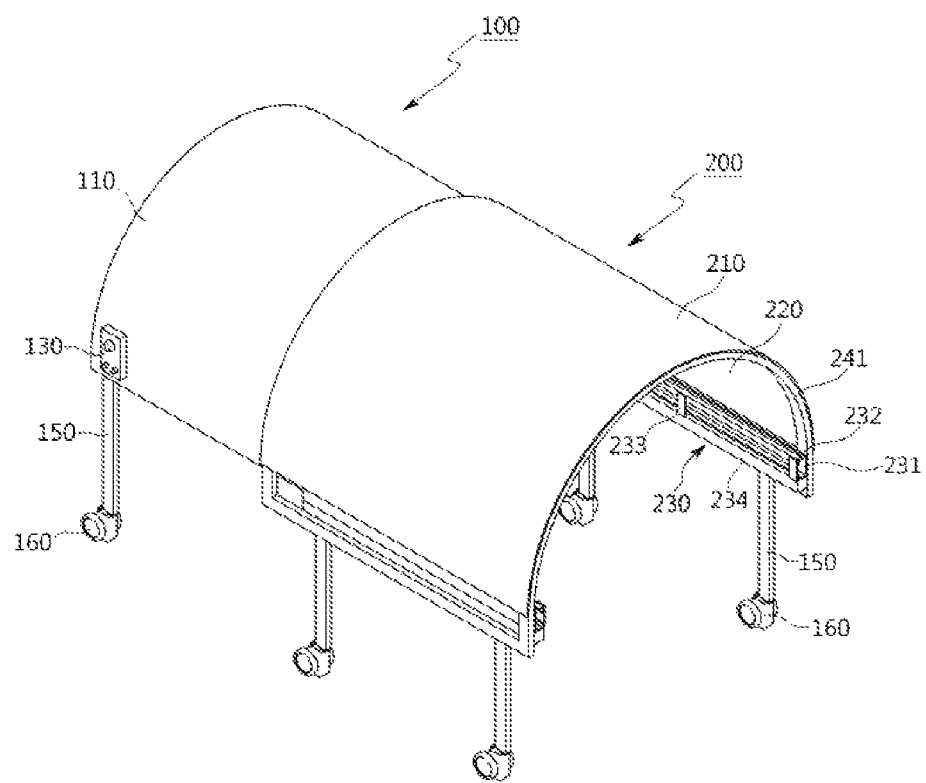
FIG. 3 is a perspective view illustrating a variable capsule-type hot-air bath apparatus of the present invention.
Figure 4:
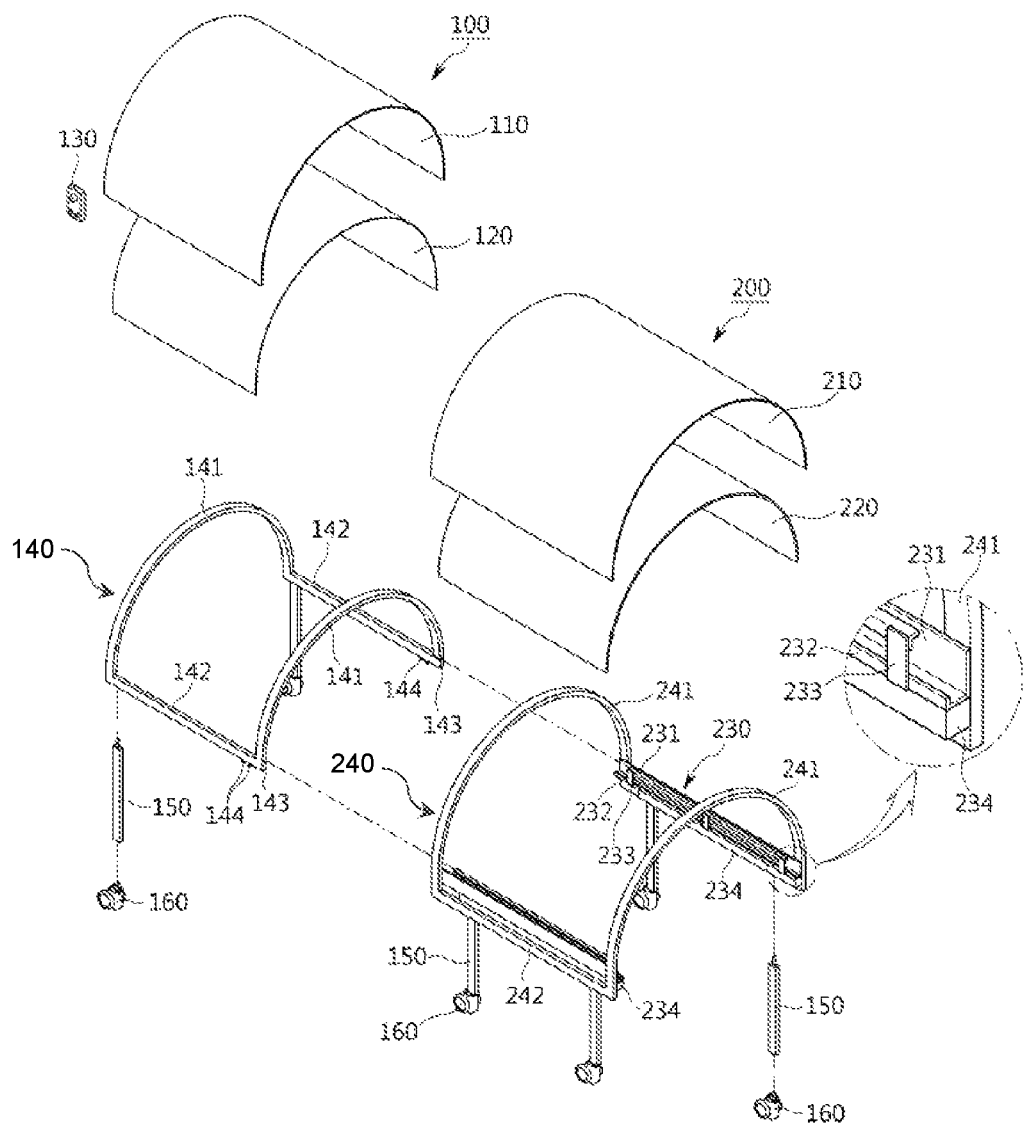
FIG. 4 is an exploded perspective view illustrating the variable capsule-type hot-air bath apparatus of the present invention.
Figure 5:
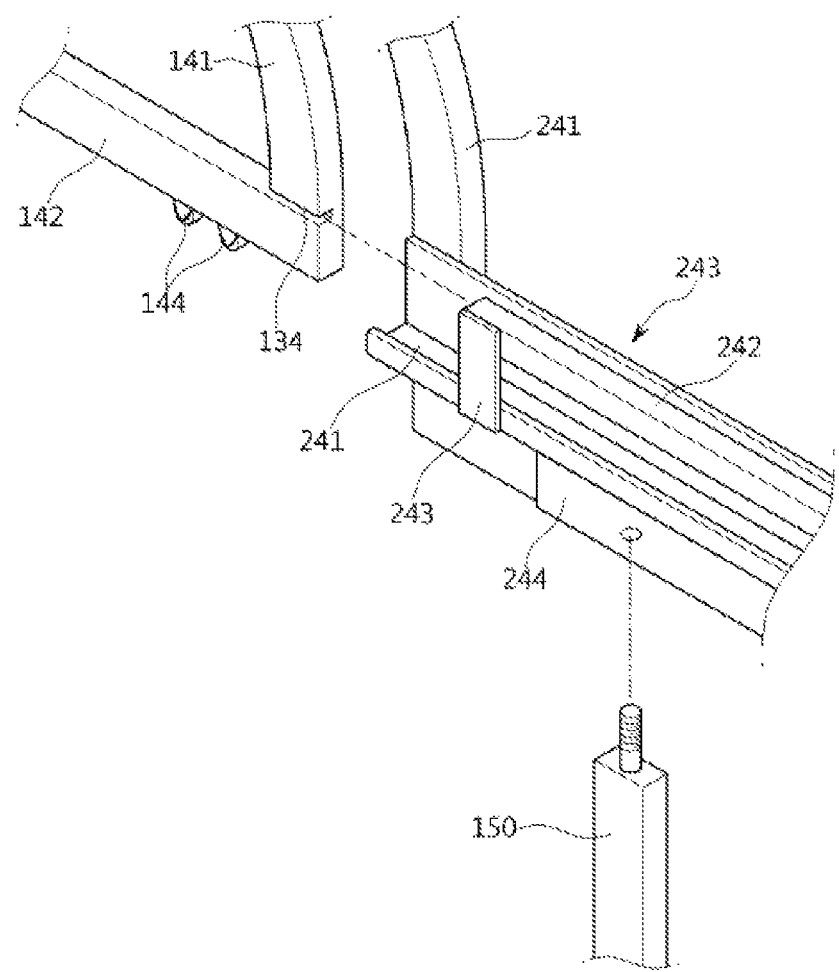
FIG. 5 is an exploded perspective view illustrating a part of the variable capsule-type hot-air bath apparatus of the present invention.
Figure 6:
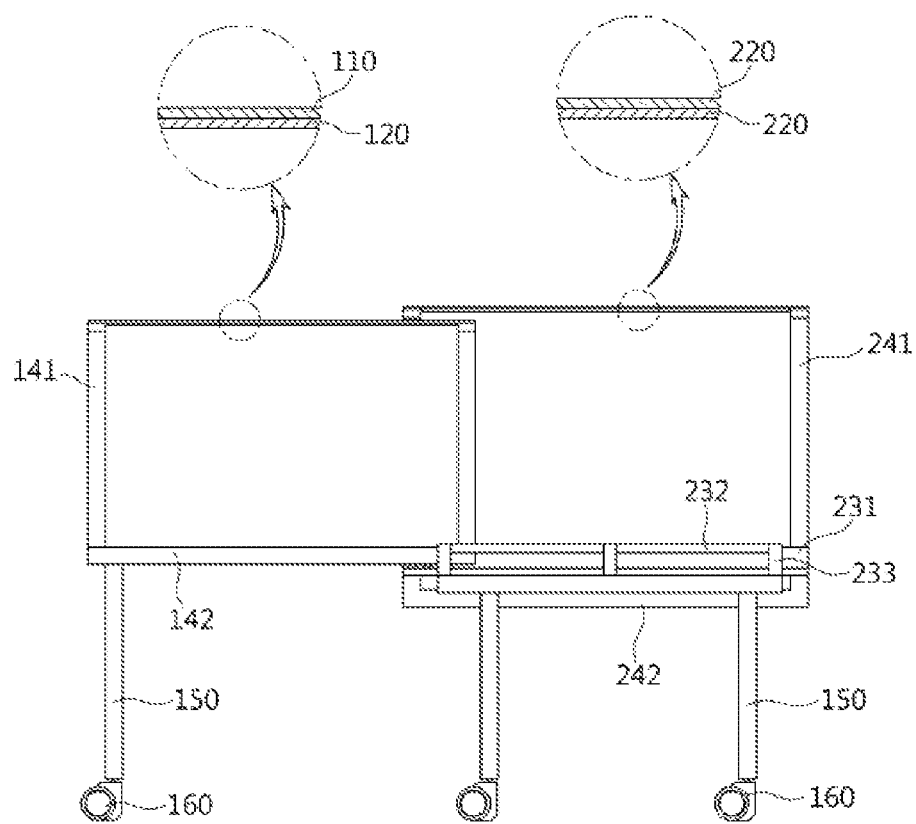
FIG. 6 is a lateral cross-sectional view illustrating the variable capsule-type hot-air bath apparatus of the present invention.
Figure 7:
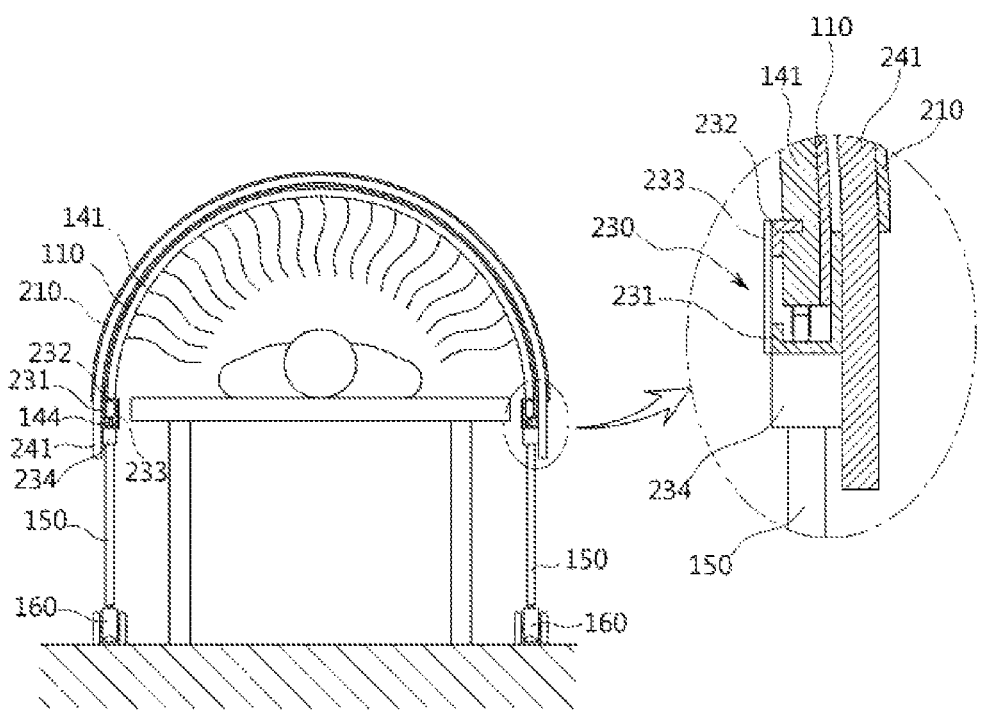
FIG. 7 is a lateral cross-sectional view illustrating a use state of the variable capsule-type hot-air bath apparatus of the present invention.

FIG. 1 is a perspective view of a related art of the present invention, FIG. 2 is a perspective view of another related art of the present invention, FIG. 3 is a perspective view illustrating a variable capsule-type hot-air bath apparatus of the present invention, FIG. 4 is an exploded perspective view illustrating the variable capsule-type hot-air bath apparatus of the present invention, FIG. 5 is an exploded perspective view illustrating a part of the variable capsule-type hot-air bath apparatus of the present invention, FIG. 6 is a lateral cross-sectional view illustrating the variable capsule-type hot-air bath apparatus of the present invention, and FIG. 7 is a lateral cross-sectional view illustrating a use state of the variable capsule-type hot-air bath apparatus of the present invention, and the variable capsule-type hot-air bath apparatus of the present invention includes: a first hot-air bath apparatus 100 including a first cover 110 covering and protecting an upper part thereof, a first film heater 120 attached to a lower part of the first cover 110 to generate heat, a first frame 140 attached and fixed to a circumference of one side of the lower part of the first cover 110 and formed in a U-shape, legs 150 coupled to the lower part of one side of the first frame by using bolts, and wheels 160 coupled to lower parts of the legs by using bolts; and a second hot-air bath apparatus 200 including a second cover 210 covering and protecting an upper part thereof, a second film heater 220 attached to a lower part of the second cover 210 to generate heat, a second frame 240 attached and fixed to a circumference of one side of the lower part of the second cover and formed in a U-shape, rail parts 230 mounted on and fixed to inner sides of both sides of the second frame 240 to make the second hot-air bath apparatus 200 smoothly move, legs 150 coupled to a lower part of one side of the second frame by using bolts, and wheels 160 coupled and fixed to the lower parts of the legs 150 by using bolts.

The first cover 110 is a plate having a predetermined thickness, and is bent in a U-shape together with the first frame shaped like a U-shape and fixed to an upper part of the first frame.

The first film heater 120 is attached to a lower part of the first cover, so that when a user controls a temperature through a temperature controller, the first film heater 120 generates a heat at an appropriate temperature to enable the user to take a hot-air bath.

The temperature controller 130 is mounted on a lower part of an external side of the first cover or the second cover to perform a control function of controlling a temperature to a user desired temperature.

The first frame 140 is formed by mounting and fixing a first U-shaped frame 141 bent in a U-shape, and first supports 142 to lower ends of both sides of the first U-shaped frame 141, and mounting and fixing another first U-shaped frame 141 to distal ends of the first supports, a guide groove 143, which helps a guide 232 formed in the rail part 230 to be coupled and move, is formed a lower part of one side of the first U-shaped frame 141, and a roller 144, which helps the second hot-air bath apparatus 200 to move when the second hot-air bath apparatus 200 moves, is formed at a lower part of one side of the first support, and a screw hole is formed in a lower part of the other side of the first support so that the leg 150 may be coupled.

The leg 150 is a frame having a predetermined length, and is provided with a bolt at an upper part thereof and provided with a screw at a lower part thereof so as to be inserted and engaged with the bolt provided at the wheel 160, so that the leg 150 may be coupled and fixed to the screw formed at a lower part of one side of the first support 142 formed in the first frame 140 by using the bolt.

The wheel 160 includes a wheel, a body supporting the wheel, and the bolt formed on an upper part of the body, and coupled and fixed to the screw formed at a lower part of the leg 150 with the bolt to facilitate a movement when moving.

The second cover 210 is a plate having a predetermined thickness, and is bent in a U-shape together with the first frame shaped like a U-shape and fixed to the upper part of the first frame.

The second film heater 220 is attached to the lower part of the first cover, so that when a user controls a temperature through the temperature controller, the second film heater 220 generates a heat at an appropriate temperature to enable the user to take a hot-air bath.

The rail part 230 includes a rail 231, of which an opened surface faces in an up direction, and a length of one-side surface is short, a guide 232 shaped like "⌐" and formed on the surface of the rail 231 having the short length, a support plate 233 attached and fixed to one side of the surface of the rail 231 having the short length and one side surface of the guide 232 to support the guide 232, and a fixing frame 234 provided with a screw hole at a lower part thereof and formed at a lower part of the rail 231 so as to be coupled and fixed with the wheel 160.

The second frame 240 is formed by fixing and mounting a second U-shaped frame 241 bent in a U-shape, and second supports 242 at lower ends of both sides of the second U-shaped frame 241, and fixing another second U-shaped frame 241 to distal ends of the second supports 242, and the rail part 230 is formed at a lower part of the inner side of the second U-shaped frame 241.

Here, a heat blocking film, such as a curtain, may also be installed on the first U-shaped frame 141 and the second U-shaped frame 241 at the external side.

The second frame 240 is formed to have a larger inner diameter of the U-shape than that of the first frame 140 and formed on the first frame to move.

Next, an operation of the variable capsule-type hot-air bath apparatus will be described in detail based on the description of a use state of the variable capsule-type hot-air bath apparatus including the aforementioned configuration.

Referring to FIGS. 3 and 4, the variable capsule-type hot-air bath apparatus of the present invention is the capsule-type hot-air bath apparatus shaped like a reverse U, and is generally divided into the first hot-air bath apparatus 100 and the second hot-air bath apparatus 200, and a length thereof may be increased and decreased according to a usage by moving the second hot-air bath apparatus 200 through the rail 230 formed in the second hot-air bath apparatus 200 for use.

Further, the wheels 160 formed at the lower parts of the legs 150 to make the variable capsule-type hot-air bath apparatus smoothly move, and the variable capsule-type hot-air bath apparatus has a simple structure, so that it is possible to easily assemble the variable capsule-type hot-air bath apparatus, thereby enabling anybody to enjoy a hot-air bath.

Referring to FIG. 5, the rail 231 is formed in the rail part 230, the guide 232 is formed at one side of the rail 231, and the support plate 233 supporting and fixing the rail 231 and the guide 232 is formed. Further, the guide groove 143 is formed at the lower part of one side of the first frame 100, the roller 144 making the first frame 100 smoothly move is formed at a lower part of the first support 142, so that when the first hot-air bath apparatus 100 and the second hot-air bath apparatus 200 are coupled, the roller 144 formed at the lower part of the first support 142 is seated on the rail 231, and the guides 232 of the rail parts 230 are inserted into the guide grooves 143 formed at both sides of the lower part of the first frame 140 to be prevented from being separated.

The coupled roller 143 is seated on the rail 231 to help the movement, and the guide 232 is inserted into the guide groove 143 to be prevented from being separated, and makes the second frame 200 straightly move when moving.

By the aforementioned structure, it is possible to easily assemble the capsule-type hot-air bath apparatus through a simple structure, costs of the capsule-type hot-air bath apparatus are decreased, and anybody can easily take a hot-air bath even in a small space, thereby improving utilization.

The exemplary embodiment of the present invention has been described, but the present invention is not limited thereto, and modifications can be made thereto without departing from the technical spirit and scope of the present invention.

INDUSTRIAL APPLICABILITY

The present invention may be used in various places, such as a bathroom, an aesthetic message shop, and home, enables a user to take a hot-air bath for a whole body and a partial body with a simple operation method of a temperature controller, it is possible to easily and simply manufacture and assemble the present invention, thereby reducing costs, and enables a user to safely and effectively take a hot-air bath, so that industrial availability thereof is high.

The invention claimed is:

1. A variable capsule-shaped hot-air bath apparatus, comprising:
a first hot-air bath apparatus (100) including a first cover (110) covering and protecting an upper part thereof, a first film heater (120) attached to a lower part of the first cover (110) to generate heat, a first frame (140) attached and fixed to a circumference of one side of the lower part of the first cover (110) and formed in a U-shape, legs (150) coupled to the lower part of one side of the first frame by using bolts, and wheels (160) coupled to lower parts of the legs by using bolts; and
a second hot-air bath apparatus (200) including a second cover (210) covering and protecting an upper part thereof, a second film heater (220) attached to a lower part of the second cover (210) to generate heat, a second frame (240) attached and fixed to a circumference of one side of the lower part of the second cover and formed in a U-shape, rail parts (230) mounted on and fixed to inner sides of both sides of the second frame (240) to make the second hot-air bath apparatus (200) smoothly move, legs (150) coupled to a lower part of one side of the second frame by using bolts, and wheels (160) coupled and fixed to the lower parts of the legs (150) by using bolts,
wherein the first cover (110) is a plate having a predetermined thickness, and is bent in a U-shape together with the first frame shaped like a U-shape and fixed to an upper part of the first frame, the first film heater (120) is attached to a lower part of the first cover, so that when a user controls a temperature through a temperature controller, the first film heater (120) generates a heat at an appropriate temperature to enable the user to take a hot-air bath, and the temperature controller (130) is mounted on a lower part of an external side of the first cover or the second cover to perform a control function of controlling a temperature to a user desired temperature, and the first frame (140) is formed by mounting and fixing a first U-shaped frame (141) bent in a U-shape, and first supports (142) to lower ends of both sides of the first U-shaped frame (141), and mounting and fixing another first U-shaped frame (141) to distal ends of the first supports, a guide groove (143), which helps a guide (232) formed in the rail part (230) to be coupled and move, is formed a lower part of one side of the first U-shaped frame (141), and a roller (144), which helps the second hot-air bath apparatus (200) to move when the second hot-air bath apparatus (200) moves, is formed at a lower part of one side of the first support, and a screw hole is formed in a lower part of the other side of the first support so that the leg (150) is coupled.

2. The variable capsule-shaped hot-air bath apparatus of claim 1,
wherein the leg (150) is a frame having a predetermined length, and is provided with a bolt at an upper part thereof and provided with a screw at a lower part thereof so as to be inserted and engaged with a bolt provided at the wheel (160), so that the leg (150) is coupled and fixed to a screw formed at a lower part of one side of the first support (142) formed in the first frame (140) by using the bolt, and the wheel (160) includes a wheel, a body supporting the wheel, and the bolt formed on an upper part of the body, and coupled and fixed to the screw formed at a lower part of the leg (150) with the bolt to facilitate a movement when moving.

3. The variable capsule-shaped hot-air bath apparatus of claim 1, wherein the second cover (210) is a plate having a predetermined thickness, and is bent in a U-shape together with the first frame shaped like a U-shape and fixed to the upper part of the first frame, the second film heater (220) is attached to the lower part of the first cover, so that when a user controls a temperature through a temperature controller, the second film heater (220) generates a heat at an appropriate temperature to enable the user to take a hot-air bath; the second frame (240) is formed by fixing and mounting a second U-shaped frame (241) bent in a U-shape, and second supports (242) at lower ends of both sides of the second U-shaped frame (241), and fixing and mounting another second U-shaped frame (241) to distal ends of the second supports (242), and the rail part (230) is formed at a lower part of the inner side of the second U-shaped frame (241); and the second frame (240) is formed to have a larger inner diameter of the U-shape than that of the first frame (140) and formed on the first frame to move.

4. The variable capsule-shaped hot-air bath apparatus of claim 1, wherein a rail (231) shaped like "└┘", of which an opened surface faces in an up direction, and a length of one-side surface is short, is formed, a guide (232) shaped like "┐" is formed on the surface of the rail (231) having the short length, a support plate (233) attached and fixed to one side of the surface of the rail (231) having the short length and one side surface of the guide (232) to support the guide (232), and a fixing frame (234) provided with a screw hole at a lower part thereof and formed at a lower part of the rail (231) so as to fix the leg (150) coupled and fixed with the wheel (160).

5. A variable capsule-shaped hot-air bath apparatus, comprising:
a first hot-air bath apparatus (100) including a first cover (110) covering and protecting an upper part thereof, a first film heater (120) attached to a lower part of the first cover (110) to generate heat, a first frame (140) attached and fixed to a circumference of one side of the lower part of the first cover (110) and formed in a U-shape, legs (150) coupled to the lower part of one side of the first frame by using bolts, and wheels (160) coupled to lower parts of the legs by using bolts; and
a second hot-air bath apparatus (200) including a second cover (210) covering and protecting an upper part thereof, a second film heater (220) attached to a lower part of the second cover (210) to generate heat, a second frame (240) attached and fixed to a circumference of one side of the lower part of the second cover and formed in a U-shape, rail parts (230) mounted on and fixed to inner sides of both sides of the second frame (240) to make the second hot-air bath apparatus (200) smoothly move, legs (150) coupled to a lower part of one side of the second frame by using bolts, and wheels (160) coupled and fixed to the lower parts of the legs (150) by using bolts,
wherein the leg (150) is a frame having a predetermined length, and is provided with a bolt at an upper part thereof and provided with a screw at a lower part thereof so as to be inserted and engaged with a bolt provided at the wheel (160), so that the leg (150) is coupled and fixed to a screw formed at a lower part of one side of the first support (142) formed in the first frame (140) by using the bolt, and the wheel (160) includes a wheel, a body supporting the wheel, and the bolt formed on an upper part of the body, and coupled and fixed to the screw formed at a lower part of the leg (150) with the bolt to facilitate a movement when moving.

6. A variable capsule-shaped hot-air bath apparatus, comprising:
a first hot-air bath apparatus (100) including a first cover (110) covering and protecting an upper part thereof, a first film heater (120) attached to a lower part of the first cover (110) to generate heat, a first frame (140) attached and fixed to a circumference of one side of the lower part of the first cover (110) and formed in a U-shape, legs (150) coupled to the lower part of one side of the first frame by using bolts, and wheels (160) coupled to lower parts of the legs by using bolts; and
a second hot-air bath apparatus (200) including a second cover (210) covering and protecting an upper part thereof, a second film heater (220) attached to a lower part of the second cover (210) to generate heat, a second frame (240) attached and fixed to a circumference of one side of the lower part of the second cover and formed in a U-shape, rail parts (230) mounted on and fixed to inner sides of both sides of the second frame (240) to make the second hot-air bath apparatus (200) smoothly move, legs (150) coupled to a lower part of one side of the second frame by using bolts, and wheels (160) coupled and fixed to the lower parts of the legs (150) by using bolts,
wherein a rail (231) shaped like "└┘", of which an opened surface faces in an up direction, and a length of one-side surface is short, is formed, a guide (232) shaped like "┐" is formed on the surface of the rail (231) having the short length, a support plate (233) attached and fixed to one side of the surface of the rail (231) having the short length and one side surface of the guide (232) to support the guide (232), and a fixing frame (234) provided with a screw hole at a lower part thereof and formed at a lower part of the rail (231) so as to fix the leg (150) coupled and fixed with the wheel (160).

* * * * *